(12) United States Patent  
Discenzo (10) Patent No.: US 6,324,899 B1  
(45) Date of Patent: Dec. 4, 2001

(54) BEARING-SENSOR INTEGRATION FOR A LUBRICATION ANALYSIS SYSTEM

(75) Inventor: Frederick M. Discenzo, Brecksville, OH (US)

(73) Assignee: Reliance Electric Technologies, LLC, Mayfield Heights, OH (US)

( * ) Notice: Subject to any disclaimer, the term of this patent is extended or adjusted under 35 U.S.C. 154(b) by 0 days.

(21) Appl. No.: 09/257,680

(22) Filed: Feb. 25, 1999

Related U.S. Application Data (63) Continuation-in-part of application No. 09/054,117, filed on Apr. 2, 1998.

(51) Int. Cl.$^7$ ............................. G01N 19/08; G21C 17/00
(52) U.S. Cl. ............................. 73/53.05; 73/10; 73/54.02; 340/631
(58) Field of Search ............................. 73/53.05, 10, 53.01, 73/54.02; 340/631, 603; 422/82.02

(56) References Cited

U.S. PATENT DOCUMENTS

| | | | |
|---|---|---|---|
| 1,996,063 | * 4/1935 | Corkran | 175/183 |
| 2,837,913 | 6/1958 | Rich et al. | 73/59 |
| 2,883,855 | * 4/1959 | Spengler et al. | 73/10 |
| 3,256,741 | 6/1966 | Wise | 73/432 |
| 3,393,553 | 7/1968 | Kleinschmidt | 73/54 |
| 3,785,196 | * 1/1974 | Smith | 73/64 |
| 4,000,656 | * 1/1977 | Moioli | 73/432 R |
| 4,007,629 | * 2/1977 | Hockstein | 73/53 |
| 4,200,541 | 4/1980 | Kinner et al. | 252/12.2 |
| 4,267,722 | * 5/1981 | Hendry | 73/10 |
| 4,443,754 | * 4/1984 | King | 324/61 R |
| 4,675,662 | 6/1987 | Kondo et al. | 340/631 |
| 4,782,332 | 11/1988 | Cipris et al. | 340/603 |
| 4,783,987 | 11/1988 | Hager et al. | 73/32 A |
| 4,792,791 | 12/1988 | Cipris et al. | 340/603 |
| 4,798,738 | 1/1989 | Yafuso et al. | 427/2 |
| 4,854,159 | * 8/1989 | Bates | 73/64 |
| 4,922,745 | 5/1990 | Rudkin et al. | 73/32 A |
| 4,926,682 | 5/1990 | Holm-Kennedy et al. | 73/54 |
| 4,935,040 | 6/1990 | Goedert | 55/197 |
| 4,941,346 | 7/1990 | Suzuki et al. | 73/54 |
| 5,001,435 | * 3/1991 | Smith | 324/671 |
| 5,004,583 | 4/1991 | Guruswamy et al. | 422/58 |
| 5,038,893 | 8/1991 | Willner et al. | 184/7.4 |
| 5,151,110 | 9/1992 | Bein et al. | 55/75 |
| 5,157,963 | * 10/1992 | Muyskens et al. | 73/53.05 |
| 5,184,505 | * 2/1993 | Van Den Berg | 73/53.05 |
| 5,199,298 | 4/1993 | Ng et al. | 73/54.01 |
| 5,200,027 | 4/1993 | Lee et al. | 156/651 |
| 5,275,258 | * 1/1994 | Bousseau | 184/6.4 |

(List continued on next page.)

OTHER PUBLICATIONS

Berkeley MicroInstruments, Microviscometer Model BMV100, (Manufacturer "specs"/ads) Aug. 1997, pp. 1–14.

*Primary Examiner*—Hezron Williams
*Assistant Examiner*—David J. Wiggins
(74) *Attorney, Agent, or Firm*—Himanshu S. Amin; Alexander M. Gerasimow; William H. Walbrun (57) ABSTRACT

A bearing-sensor integration in which one or more multi-sensor lubrication sensing devices are positioned relative to the bearing to sense in situ certain parameters of the lubricating fluid. The lubrication sensing devices may be positioned on an interior surface of a bearing raceway (i.e, the outer raceway and/or the inner raceway), the bearing's cage, sealing cover, circulating system, a compliant structure positioned within the bearing chamber, a flowgate, and/or a reservoir. The lubrication sensing device(s) may include sensors for measuring certain parameters of the lubricating fluid, such as pH, chemical characteristics, electrical conductivity, temperature and/or viscosity. A processor receives lubrication-related data from the lubrication sensing device(s), processes the lubrication-related data, and provides information relating to lubrication health and/or health of the machine employing the lubricant.

41 Claims, 7 Drawing Sheets

U.S. PATENT DOCUMENTS

| | | | |
|---|---|---|---|
| 5,359,881 | 11/1994 | Kalotay et al. | 73/54.06 |
| 5,372,033 * | 12/1994 | Jackson et al. | 73/53.05 |
| 5,377,531 * | 1/1995 | Gomm | 73/53.05 |
| 5,388,442 * | 2/1995 | Kumar et al. | 73/10 |
| 5,417,821 | 5/1995 | Pyke | 204/153.1 |
| 5,418,058 | 5/1995 | Li et al. | 428/327 |
| 5,485,491 | 1/1996 | Salnick et al. | 376/245 |
| 5,487,313 | 1/1996 | Johnson | 73/863.71 |
| 5,540,086 * | 7/1996 | Park et al. | 73/53.05 |
| 5,572,328 | 11/1996 | Fouckhardt et al. | 356/440 |
| 5,581,028 | 12/1996 | Barth et al. | 73/204.26 |
| 5,614,830 | 3/1997 | Dickert et al. | 324/553 |
| 5,633,809 | 5/1997 | Wissenbach et al. | 364/510 |
| 5,644,395 | 7/1997 | Folta | 356/246 |
| 5,646,039 | 7/1997 | Northrup et al. | 435/287.2 |
| 5,660,728 | 8/1997 | Saaski et al. | 210/251 |
| 5,662,165 | 9/1997 | Tubel et al. | 166/250.01 |
| 5,679,883 * | 10/1997 | Wedeven | 73/10 |
| 5,789,665 * | 8/1998 | Voelker et al. | 73/53.05 |
| 5,817,928 * | 10/1998 | Garvey, III et al. | 73/53.05 |
| 5,852,229 | 12/1998 | Josse et al. | 73/24.06 |
| 5,933,016 * | 8/1999 | Kauffman et al. | 324/698 |
| 5,968,371 * | 10/1999 | Verdegan et al. | 210/739 |

* cited by examiner

BEARING-SENSOR INTEGRATION FOR A LUBRICATION ANALYSIS SYSTEM

RELATED APPLICATIONS

This application is a continuation-in-part of copending U.S. patent application Ser. No. 09/054,117 filed Apr. 2, 1998 and entitled MICRO VISCOSITY SENSOR AND LUBRICATION ANALYSIS SYSTEM EMPLOYING THE SAME, the entire disclosure of which is hereby incorporated by reference.

TECHNICAL FIELD

The present invention generally relates to a lubrication analysis system and more particularly to a bearing-sensor integration for such a system.

BACKGROUND OF THE INVENTION

Dynamoelectric machines such as motors and generators are widely employed in industrial and commercial facilities. Many facilities operate several hundred or even thousands of such machines concurrently and these machines are often integral components of large interdependent processes. Accordingly, the machines are each depended upon for prolonged consistent operation whereby it is extremely advantageous to provide reliable failure prediction information. Of particular relevance in the present invention are bearing-related failures and, more particularly, failures related to lubrication problems in antifriction bearings. Diagnostic studies have consistently reflected that bearing-related failures are a substantial cause (about 42% of reported failures) of motor failures.

An antifriction bearing is designed to constrain rotary or linear motion while minimizing wear and other losses such as friction. Examples of this type of bearing are sleeve bearings, hydrodynamic bearings, and rolling element bearings. The most prevalent bearing type found on medium and low horsepower (e.g. fractional to 500 hp) motors are rolling element bearings such as ball bearings. To this end, typical antifriction bearings normally include a bearing housing defining an annular chamber and a plurality of rolling elements retained within the chamber. The bearing housing typically includes two annular components known as raceways, and more particularly an outer raceway and an inner raceway having interior surfaces which form the radial walls of the bearing chamber. (In the context of the present invention, "interior" corresponds to the relation of the surface relative to the chamber.) For example, the outer raceway may be mounted to a machine (e.g., a motor) and is intended to remain stationary relative thereto, while the inner raceway supports a rotating member (e.g., the motor's rotor or shaft).

The rolling elements may be either balls or rollers and the bearing may include one or more rows of such rolling elements. A cage is usually provided to retain the rolling elements in their correct relative positions so that they do not touch one another and to provide some guidance for the rolling elements. Also a lubricating fluid, such as oil or grease, is contained within the bearing chamber to reduce the friction between the components and also assist in the dissipation of heat. The top and bottom (or axial) ends of the chamber are sealed by the mounting structure or by sealing covers to maintain the lubricating fluid within the bearing chamber and/or keep dirt or other contaminants out. An antifriction bearing may include a circulating system to inject and/or drain lubricating fluid into the bearing chamber.

The loss of lubricating effectiveness will result in accelerated wear of the bearing elements, additional heat generation due to frictional effects, higher levels of vibration and potential impact loading due to metal-to-metal contact, and accelerated degradation of lubricant health due to higher levels of temperature, metal particulate contamination, and higher loading/shear levels.

Needless to say, the health of lubrication is a significant factor in the overall operation of an antifriction bearing. Accordingly, it is essential that the lubrication of an antifriction bearing be properly provided, protected, and maintained. Initially, it is important that the correct lubricating fluid be provided for the antifriction bearing. Also, it is critical that an adequate amount of lubricating fluid be maintained in the bearing. Likewise, it is crucial that contaminants (such as water, rust, and other contaminations) not contaminate the lubricating fluid. Moreover, when the lubricating fluid is continuously exposed to elevated temperatures, accelerated speeds, high stress/loads, and an oxidizing environment, the lubricating fluid will inevitably deteriorate and lose its lubricating effectiveness.

Also, when machinery is re-lubricated by applying additional lubricant, the addition of a different, incompatible lubricant will result in considerably diminished lubricating effectiveness. The result may be accelerated bearing wear beyond what would occur if no additional lube was added. The loss of bearing lubricant due to a seal failure is important to detect to prevent accelerated bearing wear and to avoid a "dry" running condition. It is also important to detect the loss of bearing lubricant in critical manufacturing processes such as pharmaceutical, medical products, and food products manufacturing. Loss of lubricant could result in a contaminated product or worse a contaminated product which remains undetected before reaching the consumer.

Lubrication-related problems tend to be insidious. There is often only a minor degradation of the lubricating fluid at the beginning. However, continued operation of the machine results in even greater heat generation and accelerated degradation of the lubricating fluid. Left untreated, the bearing will eventually fail leading to substantial machinery damage. In short, the continued operation of a degraded bearing will generally destroy machinery beyond just the bearing and repair costs can be extremely high, not to mention the catastrophic and potentially unsafe conditions such a failure creates. Unfortunately, many lubrication-related problems are only recognized after irreparable destruction has occurred to not only the bearing, but the machine itself. For example, some lubricant problems eventually result in a bearing seizing up and the continued rotary motion destroying the rotating shaft or the bearing mounting. Alternatively uncontrolled vibration could occur, resulting in destruction of machinery and buildings.

The previous discussion presented bearings and lubrication issues from the standpoint of motor-mounted bearings. The problems identified and the need for lubricant health information applies to bearings found in a wide range of machinery, including machinery connected to a motor (driven equipment), land-based vehicles, shipboard systems and aircraft systems. This includes bearings in internal combustion engines, engine accessories, gears and gear systems, wheels, linear slides, conveyors, rollers, and pillow blocks for example.

Accordingly, an early diagnosis and cure of lubrication-related problems can be extremely beneficial in reducing machine down-time, repair cost, inconvenience, and even hazardous situations. For this reason, conservative lubricant changing schedules (where the lubricating fluid is changed well before any degradation is expected to occur) are sometimes well worth what may be viewed as wasted labor and wasted lubricating fluid and un-necessary machinery downtime if needed. Other times, however, the cost and labor associated with replacing adequate functioning lubricating fluid cannot be justified. Additionally, the more frequent the changes, the higher the possibility that the wrong lubricating fluid will be provided and/or other changing mistakes will be made such as over lubricating equipment. More importantly, each lubrication situation seems to be relatively unique in view of the almost countless factors that can contribute to lubrication degradation. As such, in many situations, a lubricating fluid will reach at least the initial stages of breakdown or contamination well before even a conservative scheduled change.

The potential damage associated with inadequate bearing lubrication and the uniqueness of each lubrication situation has led many industries to adopt programs of periodic monitoring and analyzing of the lubricating fluid. In some programs, for example, the condition of the lubrication is determined by measuring a dielectric constant change in the lubricating fluid. In other programs, for example, the condition of the lubrication is instead determined by recording historical thermal readings. Unfortunately, these programs measure only a single parameter, such as temperature over time, require the use of the same lubricating fluid, and/or assume no machinery malfunctions between measurements. Furthermore, extensive lubrication monitoring and analysis techniques are not performed in situ and typically involve extracting a sample of the lubricating fluid and then analyzing this sample using laboratory equipment. As such, these sampling techniques only provide a narrow, periodic view of lubrication quality and/or health whereby accurate lubrication health assessment and lifetime prediction is virtually impossible to achieve. Moreover, the manpower required to extract the lubricant samples necessarily limits the frequency of sampling, not to mention the introduction of human error into the extraction process. In some situations, lubricating oil may be extracted from machinery and put in glass bottles in front of a light source. A visual inspection is made after the material had settled.

Accordingly, a need remains for a lubrication analysis system which takes into account a plurality of parameters relating to lubricant health and which allows in situ monitoring of lubrication within its operating environment. With specific attention to the collection of data, a need remains for the successful integration of a multi-element lubrication sensing device into a bearing to provide meaningful data relating to the health of the lubrication.

SUMMARY OF THE INVENTION

The present invention provides a lubrication analysis system which takes into account a plurality of parameters relating to lubrication health and which allows in situ monitoring of lubricating fluid within its operating environment. More particularly, the present invention provides a successful integration of multiple sensors into a bearing whereby meaningful data is provided relating to the health of the lubrication. Even more particularly, the present invention provides a bearing-sensor integration in which one or more sensing devices are positioned relative to the bearing to sense in situ certain parameters of the lubricating fluid. The sensing devices may be mounted to an interior surface of a bearing raceway (e.g., the outer raceway and/or the inner raceway), the bearing's cage, sealing cover, circulating system, a compliant structure positioned within the bearing chamber, a flowgate, and/or a reservoir. The bearing-sensor integration may further comprise a transport mechanism that transports a portion of the lubricating fluid towards the sensing device, such as wiper arm and/or a paddle wheel.

The sensing device(s) include(s) sensors for measuring certain parameters of the lubricating fluid, such as pH, chemical characteristics, optical characteristics, electrical conductivity, temperature and/or viscosity. The device(s) may preferably be made by integrated circuit-like microfabrication techniques that accommodate automatic batch production whereby the sensing devices may be economically manufactured. Additionally, and more importantly (at least from a non-economic point of view), the microfabrication techniques allow lubrication sensing devices to be made of a reduced size while still providing superior sensing capabilities. This reduction in size (without a sacrifice of accuracy) allows in situ monitoring of lubricating fluid within its operating environment as compared to extracting a sample and/or testing the lubricant at a remote site. The sensors may be formed on one or both sides of a silicon base and/or a flexible base, or alternatively may be formed directly on the bearing, such as on the bearing raceway.

In the lubrication analysis system according to the present invention, a processor receives lubrication-related data from the sensing device(s), processes the lubrication-related data, and provides information relating to lubrication health. In this manner, the system may determine the present health of the lubrication so that any problems may be detected at an early stage and corrected before any damage occurs. Moreover, the system allows lubrication data to provide insight into the early onset of mechanical faults independent from inadequate lubrication. For example, a sudden increase in debris, contaminants and/or temperature can be indicative of excessive loading, seal failure, or other mechanical problems even if the absolute value of these increases are within an acceptable range for the lubricant itself.

One aspect of the present invention relates to a bearing-sensor integration including a bearing and at least one lubrication sensing device. The bearing includes a bearing housing defining a chamber, a plurality of rolling elements retained within the chamber, and lubricating fluid contained within the chamber. The lubrication sensing device includes a plurality of different sensors. The lubrication sensing device is positioned relative to the bearing so that the sensors sense in situ different parameters of the lubricating fluid.

Another aspect of the present invention relates to a bearing lubrication analysis system. The system includes a bearing employing a lubricant; first sensing means for sensing a first parameter of the lubricant; second sensing means for sensing a second parameter of the lubricant; and processing means operatively coupled to the first and second sensing means, the processing means analyzing the sensed lubricant parameters.

Still another aspect of the present invention relates to a bearing-sensor integration, including: a bearing employing a lubricant; and a lubricant sensor integrated with the bearing such that at least a portion of the sensor is in contact with the lubricant, the lubricant sensor further including: a pH sensor; a chemical sensor; a conductivity sensor; and a temperature sensor.

Yet another aspect of the present invention relates to a method for determining the health of a bearing lubricant, comprising the steps of: using a lubricant sensor operatively coupled to a bearing to collect in situ data relating to at least one lubricant parameter, the at least one lubricant parameter being selected from a group including: pH, chemistry, conductivity, temperature and viscosity; using a processor operatively coupled to the lubricant sensor to analyze the data and render a health assessment of the lubricant.

Another aspect of the present invention relates to a drain plug/lubricant sensor combination; including: a drain plug of a lubricant reservoir, the drain plug including a first end and a second end; a lubricant sensor coupled to the surface of the first end of the drain plug, at least a portion of the lubricant sensor being in contact with lubricant, the lubricant sensor including a pH sensor, a chemical sensor, a conductivity sensor, and a temperature sensor.

These and other features of the invention are fully described and particularly pointed out in the claims. The following descriptive annexed drawings set forth in detail certain illustrative embodiments, these embodiments being indicative of but a few of the various ways in which the principles of the invention may be employed. Other objects, advantages and novel features of the invention will become apparent from the following detailed description of the invention when considered in conjunction with the drawings.

DETAILED DESCRIPTION OF THE DRAWINGS

Figure 1:
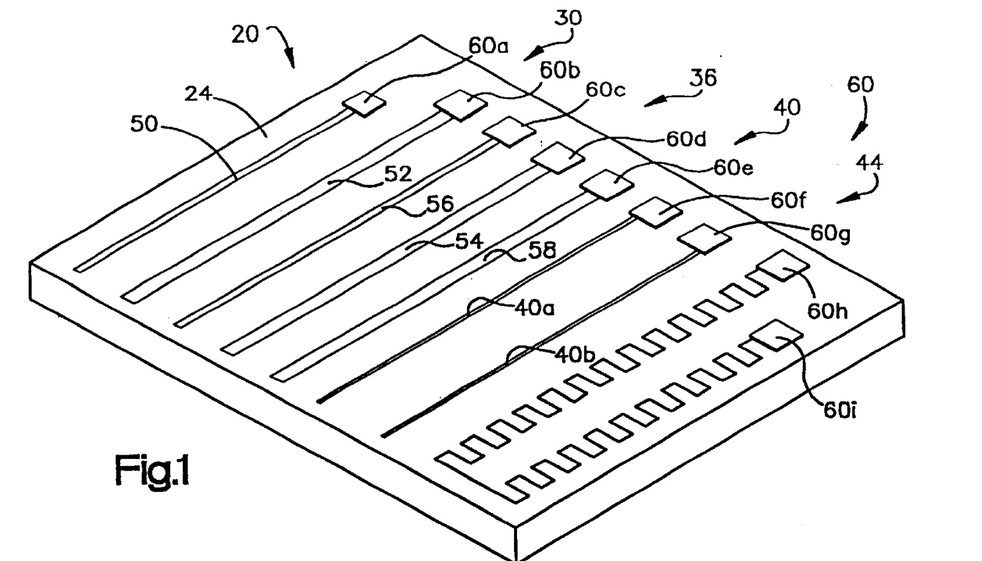
FIG. 1 is a perspective view of an exemplary lubrication sensing device which may be used in a bearing-sensor integration according to the present invention.

Referring now to the drawings in detail, and initially to FIG. 1, an exemplary lubrication sensing device 20 is shown in perspective view. According to the present invention, the lubrication sensing device 20 is integrated into a bearing 22 (FIGS. 4a, 4b and 5–13). This bearing-sensor integration allows in situ lubrication readings to be obtained at a substantially high data sampling rate whereby accurate up-to-date, real-time, continuous data analysis of lubrication health may be provided. In this manner, lubrication maintenance can be scheduled to correspond with the state of the lubrication and/or the processed data can be compiled for trend analysis and forecasting. Lubrication maintenance may be reliably scheduled based on the projected future state of the bearing lubricant. Performing maintenance based on projected future state of the lubricant enables industries to implement effective condition based maintenance programs.

Although the present invention is primarily described in the context of ball bearing systems, it is to be appreciated that the present invention applies to substantially all rolling element bearings (e.g., roller bearings, cylindrical bearings, taper roller bearings, double row ball bearings sleeve bearings, hydrodynamic bearings). The scope of the present invention as defined by the hereto appended claims is intended to include such bearing applications.

The illustrated lubrication sensing device 20 may be made in accordance with integrated circuit-like fabrication techniques thereby making it possible for the device 20 to have a relatively small geometry, such as a substantially flat square shape having an approximately 4 mm$^2$ area or smaller. Thus, the lubrication sensing device 20 is desirable for bearing-sensor integrations wherein space is at a premium but accuracy, reliability, and sensitivity of measured data are equally as important. Furthermore, the integrated circuit-like fabrication procedures allow the efficient and economic manufacture of large batches and/or high production yields.

The illustrated lubrication sensing device 20 includes a semiconductor base 24, made of silicon or any other suitable material, and a plurality of sensors formed on the base 24. The illustrated sensors include a pH sensor 30 (to determine ionic conditions); a chemical sensor 36 (to determine the presence of chemical contaminants); an electrical conductivity sensor 40 (to determine the presence of metal/water contaminants); and a temperature sensor or detector 44 (to determine temperature and facilitate determining viscosity). The pH sensor 30 includes a reference electrode 50 and a pH electrode 52. The chemical sensor 36 includes a reference electrode 54, a working electrode 56, and a counter electrode 58. The electrical conductivity sensor 40 includes two metal electrodes 40a and 40b. The temperature sensor or detector 44 is essentially a pattern (having known geometric dimensions) formed on the base 24 from a material having an electrical conductivity that varies within the expected range of temperatures. The lubrication sensing device 20 further comprises respective sets of contact pads 60a–60i coupled to the sensors 30, 36, 40 and 44.

Depending on the particular bearing-sensor integration, the illustrated lubrication sensing device 20 may be acceptable and even preferable. However, other lubrication sensing devices are possible with and contemplated by the present invention, and may be more advantageous in certain bearing-sensor integration situations. For example, depending on the desired data collection, certain sensors may be omitted, certain sensors may be repeated, the sensitivities of replicated sensors sealed to cover a wide dynamic range, and/or different types of sensors may be added. For a specific example, a viscosity sensor may be provided that works in conjunction with the temperature sensor 44 to measure the lubricant's viscosity. (A suitable viscosity sensor is shown and described in U.S. patent application Ser. No. 09/054,117, entitled MICRO-VISCOSITY SENSOR AND LUBRICATION ANALYSIS SYSTEM EMPLOYING THE SAME, the entire disclosure of which has been or is hereby incorporated by reference.)

Additionally or alternatively, instead of the rigid silicon substrate base 24, the sensors 30, 36, 40 and 44 could be fabricated on a flexible substrate material to accommodate, for instance, in connection with the bearing-sensor integrations shown in FIGS. 4–7. Also, the sensors 30, 36, 40, and 44, could be located on both sides of the rigid or flexible substrate base 24 as might be desirable in, for instance, in the bearing-sensor integration shown in FIG. 9. Alternatively, the sensors 30, 36, 40, and 44 could be "printed" on the bearing 22 itself (e.g., using techniques such as sputtering) to eliminate the need for the substrate 24 as may be advantageous in, for instance, the bearing-sensor integrations shown in FIGS. 4-8. Moreover, as is discussed in more detail below, a processing unit may be incorporated into the lubrication sensing device 20 to perform data acquisition, analyzer functions, communications, afford self diagnosis, establish lubricant health, predict when lubricant service is required, and/or verify feasible operating regimes.

Figure 2:
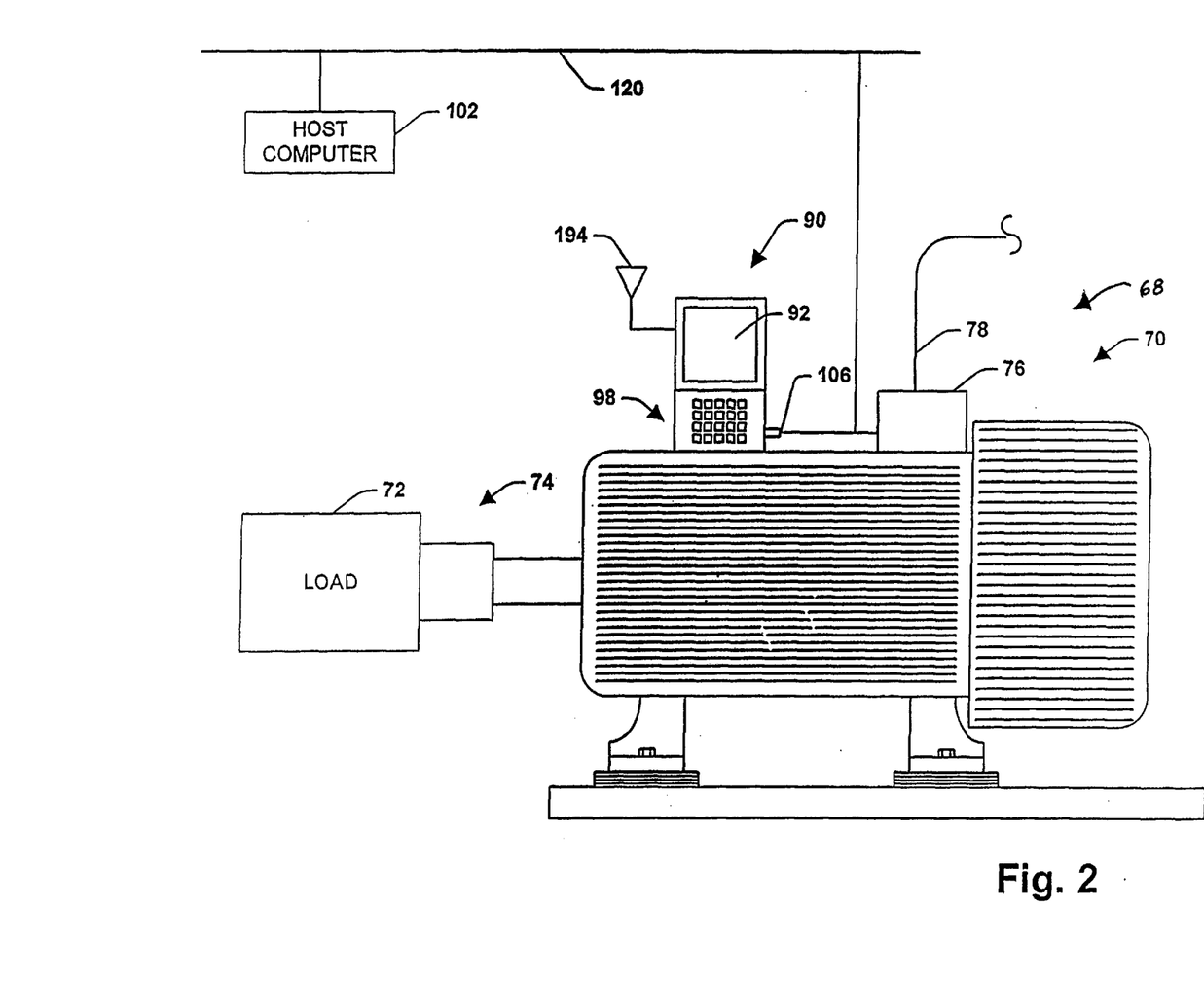
FIG. 2 is an exemplary environment for the bearing-sensor integration according to the present invention is schematically shown.

Referring now additionally to FIG. 2, an exemplary environment for the bearing-sensor integration according to the present invention is schematically shown. In the illustrated example, a lubrication analysis system 68 is used in conjunction with a motor 70. The illustrated motor 70 may be a three-phase AC induction motor that drives a load 72 through a shaft coupling 74 and a junction box 76 is provided to receive and tie power supply lines. In any event, the motor 70 includes one (and probably more) antifriction bearings. For example, two antifriction bearings would typically be used to mount the motor's rotor and/or shaft 74 to the motor end brackets. The system 68 measures, determines, analyzes, monitors, and/or controls the lubrication health of the bearing based on readings received from one or more lubrication sensing devices 20 embedded in the bearings.

The lubrication analysis system 68 includes an analyzer 90 which, in the illustrated embodiment includes a display 92 for displaying lubrication-related information and a keypad 98 for entering data and/or commands. The system 68 further comprises a host computer 102 that makes determinations as to the health of the lubrication, this determination preferably including performing data fusion of the sensed lubricant data (e.g., pH, chemical, conductivity, temperature) to facilitate condensing, combining, trending, forecasting, evaluating and interpreting the sensed data.

The analyzer 90 includes a communications port 106 or other interface for receiving information from the lubrication sensing device(s) 20. Once the analyzer 90 (and more particularly its processor 130, introduced below) has processed the lubrication-related data, it is sent to the host computer 102 via a network backbone 120 (which may be hardwired and/or wireless). In this manner, the highly accurate and up-to-date information may be provided regarding the health of the lubrication. Data may be combined from multiple bearings in the host computer 102 and lubrication health and future lubrication requirements may be communicated to plant maintenance, job scheduling, routing, and inventory systems as appropriate.

Figure 3:
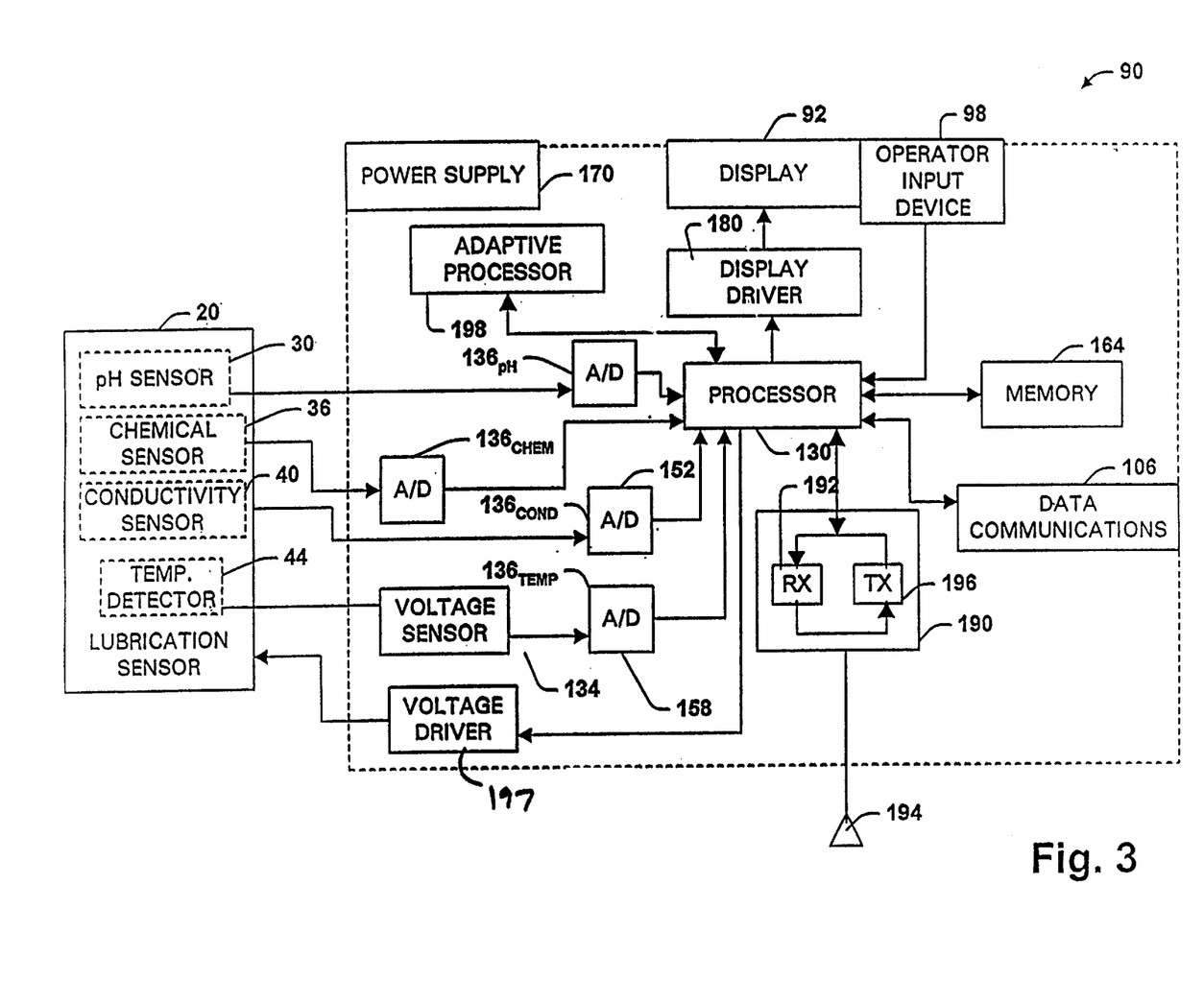
FIG. 3 is a block diagram showing the interaction of the lubrication sensing device and a lubrication analyzer.

Referring now to FIG. 3, further details of the analyzer 90, and its informational connection to the lubrication sensing device 20, are schematically shown. The lubrication analyzer 90 includes a processor 130 which analyzes information received from the lubrication sensing device 20. To this end, the pH sensor 30, the chemical sensor 36, and the electrical conductivity sensor 40 are directly coupled to A/D converters $136_{pH}$, $136_{chem}$, and $136_{cond}$, respectively. The temperature sensor (or detector) 44 is coupled to the A/D converter $136_{temp}$. The sensors 30, 36, 40, and 44 are each operatively coupled to the processor 130 via respective A/D converters 136.

The lubrication analyzer 90 includes a memory 164 that stores program code, base-line information (e.g., nominal temperature, acceptable pH, expected electrochemistry, re-lube information, loading information, duty cycle data, and appropriate viscosity values), machine specific data, acceptable error bounds/deviations, historical lubricant parameter data, and/or recommended corrective action. The lubrication analyzer 90 may also include a power supply 170 (that provides power to the processor 130, sensors and other components), a display driver circuit 180 (that couples the processor to the display 92), RF section 190 (that includes a receiver 192, an antenna 194, a transmitter 196 that transmits and receives signals), a voltage driver 197 (that provides the desired voltage to the lubrication sensing device 20), and/or an adaptive processor 198 (that analyzes the health state of the lubrication).

The lubrication analysis system 68 is designed to provide highly accurate and up-to-date information regarding the health of the lubrication. Additionally, this system will compare known lubricant health with acceptable parameters and projected lubricant aging to establish a recommended maintenance action and when this maintenance must be performed. This information is then communicated to an operator or other computer system as appropriate. Depending on the particular analysis situation and/or the specific bearing-sensor integration, the above-described lubrication analysis system 68 may be acceptable and even advantageous in certain situations. However, other lubrication analysis systems are possible with and contemplated by the present invention, and may even be preferable in certain bearing-sensor integrations according to the present invention.

For example, all of the processing functions (data analysis, lubricant state estimation, health determination, etc.) performed by the host computer 102 in the illustrated embodiment could instead be performed by the processor 130 of the lubrication analyzer 90. In this arrangement, the processed results could be transmitted to a portable computer temporarily tied to the lubrication analyzer 90 and/or transmitted to a remote control computer. Additionally or alternatively, the processed results could be displayed locally on the analyzer display screen 92.

For another example, the lubrication analyzer 90 could be located remotely from the motor 70 or the host computer 102 could carry out substantially all of the lubrication analyzer functions performed by the processor 130 in the illustrated system 68. Another option is to integrate the lubrication analyzer 90 (absent certain components, such as the display 92 and the keypad 98) onto the same base 24 as the lubrication sensing device 20 and/or the bearing 22 to provide for a substantially autonomous lubrication analysis system that performs analyzer functions, affords self diagnosis, and verifies feasible operating regimes.

For a further example, the transmittal of the readings by the sensors 30, 36, 40, and 44 could be modified to fit a particular bearing-sensor integration. In the illustrated lubrication analysis system 68, the analyzer 90 includes the communications port 106 or other interface for receiving information from the lubrication sensing device(s) 20. However, with certain bearing-sensor integrations, such as those shown in FIGS. 6 and 7, wireless sensor technology may be preferred. Additionally or alternatively, in certain bearing-sensor integrations, such as that shown in FIG. 7, an intercommunication between sensors 20 (certain sensing devices 20 relaying information to other sensing devices which then transmit the relayed information to the lubrication analyzer 90) may be the preferred transmittal procedure. To accomplish this wireless technology, low cost integrated silicon RF technology may be coupled to the on-board processor 130. As a further improvement, a magnetic field may be attached to a rotating component of the bearing 22 (such as its inner raceway 210, introduced below), to make the lubrication sensing device 20 self-powering in a flow scavenging sense that takes advantage of such generated rotating magnetic fields.

For a still further example, the lubrication analysis system 68 could additionally initiate automatic correction procedures. For instance, if the bearing 22 includes a forced lubrication system (such as the system 220 introduced below and shown schematically in FIG. 10), the injection or draining of lubricating fluid could be automatically controlled based on the current lubrication health analysis. Specifically, the detection of low levels of lubricant could automatically trigger the injection, of fresh lubricant until an adequate level is reached. The presence of an unacceptable amount of contaminants could trigger a flushing of lubricant to decontaminate the bearing environment. Additionally or alternatively, additives (such as anti-oxidant desiccant substances) could be automatically introduced to stabilize lubrication performance or even to provide survival lubrication performance during conditions of extreme wear, temperature, duty or mission critical applications. By introducing prescribed amounts of additives, lubricant health assessment may be enhanced by monitoring the rate of degradation of the new material. It is also noted that while the lubrication analyzer 90 preferably performs a plurality of functions relating to lubrication health, the processor 130 could be employed for the sole purpose of doing an emergency shut-down of the motor 70 when lubrication conditions approach a critical level.

Referring now to FIGS. 4–15, various bearing-sensor integrations according to the present invention are schematically shown. The bearing 22 is a ball bearing roller bearing of a conventional design and may be viewed as comprising a housing 202 defining a chamber 204 and a plurality of rolling elements 206 (ball bearings in the illustrated embodiment) within the chamber 204. The bearing housing 202 includes an outer raceway 208 and an inner raceway 210 having interior surfaces which form the radial walls of the annular chamber 204. (In the context of the present invention, "interior" corresponds to the relation of the surface relative to the chamber 204.) In the illustrated embodiment, the outer raceway 208 is mounted to the machine (e.g., the motor 70 end bracket) and is intended to remain stationary relative thereto, while the inner raceway 210 supports a rotating member (e.g., the shaft 74). Note, the stationary and rotating elements may be reversed without altering the application of the proposed concept. That is, the inner race may be fixed and the outer race may rotate, for example, as typically occurs in an automobile front wheel bearing.

Figure 9:
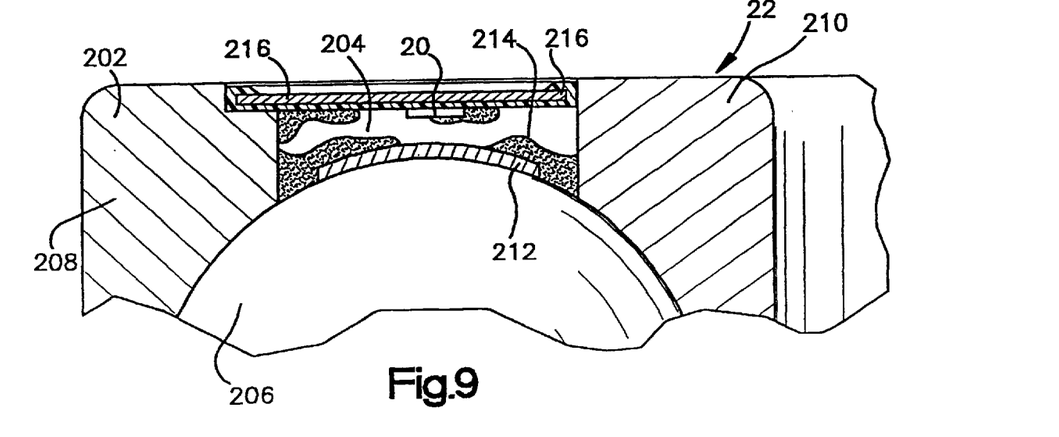

The bearing 22 further includes a cage 212 to retain the rolling elements 206 in their correct relative positions within the chamber 204 and to provide some guidance during the rotation of the inner raceway 210. Also, a lubricating fluid 214, such as oil or grease, is contained within the bearing chamber 204 to reduce the friction between the components and also assist in the dissipation of heat. The top and bottom (or axial) ends of the chamber 204 are sealed by sealing covers (e.g. bearing seals, bearing shields, or the bearing mounting structure) 216 to maintain the lubricating fluid 214 within the bearing chamber 204. (FIG. 9.) The sealing covers 216 may be, for example, washer-shaped members made of felt, leather, plastic, metal, or other suitable materials to seal the annular space between the adjacent axial surfaces of the outer raceway 208 and the inner raceway 210.

Figure 10:
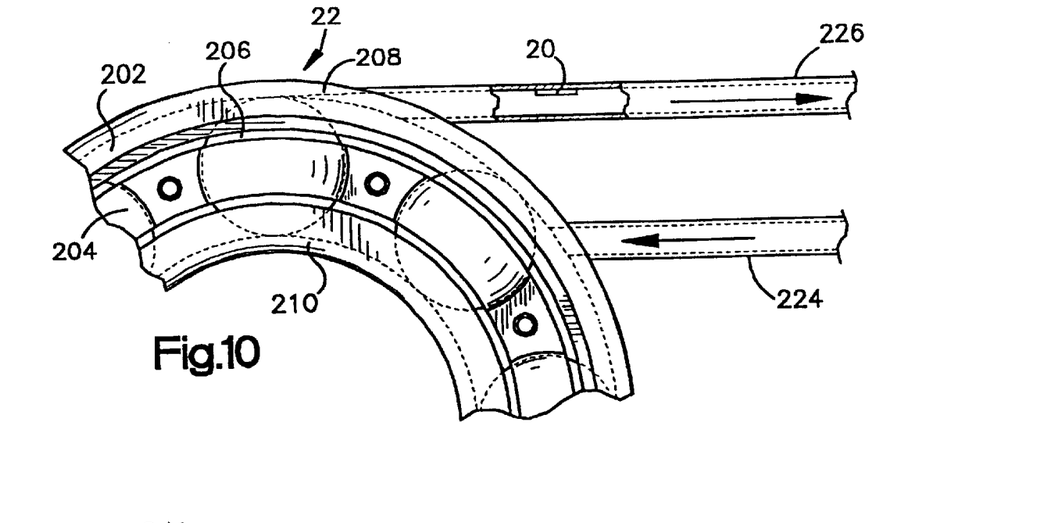

The bearing 22 may include an inlet pipe 224 through which fresh lubricating fluid or additive is pumped into the bearing chamber 204. (FIG. 10.) The inlet pipe 224 may be attached to a pump or pressurized vessel which automatically introduces fresh lubrication fluid 21 4 into the chamber 204 and an outlet pipe 206 may be provided to automatically drain the lubricating fluid 214 therefrom. (FIG. 10.) The introduction of fresh lube or additive is performed using a small activator integrated with the lube analyzer system. Alternatively, the inlet pipe 224 may be plugged at one end with, for instance, a threaded cap 228 (FIGS. 11 and 12) which may removed for introduction of fresh lubrication fluid. As another alternative, the sensor may be integrated with the grease and/or drain fitting used in conventional re-lubricated bearing systems.

Figure 4A:
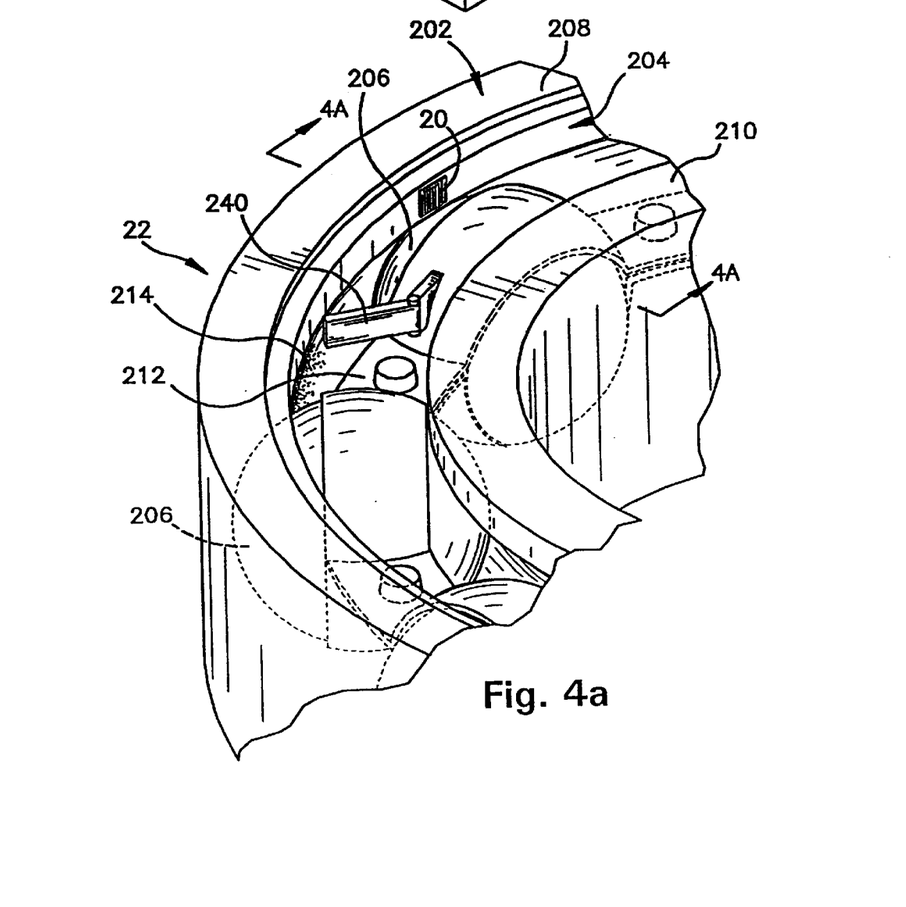
FIGS. 4a, 4b and 5–15 are schematic illustrations of various bearing-sensor integrations according to the present invention.
Figure 4B:
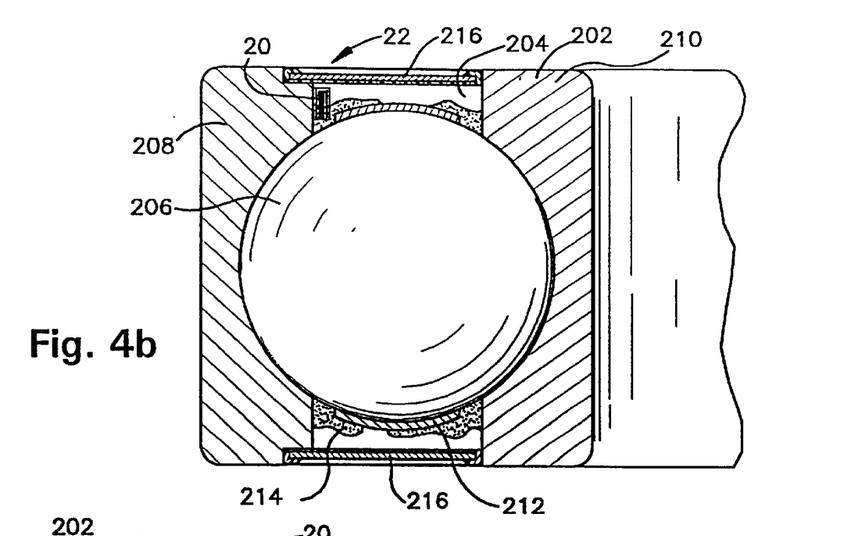

Referring now particularly to FIGS. 4a and 4b, one bearing-sensor integration according to the present invention is shown. In this embodiment, the lubrication sensing device 20 is mounted on an interior surface of the outer raceway 208. Preferably, a small area (about 1 to 4 mm$^2$) is machined in the inner surface of the raceway 208 to provide a mounting location for the sensor 20. The mounting location is preferably in close proximity to the center circular contact path of the ball bearings 206 on the outer raceway 208, but slightly off-center relative thereto to avoid direct contact. Preferably, a wiper arm 240 (such as miniature windshield wiper) has one end pivotally attached to the bearing 22 (and particularly the cage 212) whereby as the cage 212 rotates, unattached portions of the wiper arm 240 are pivoted to transport a changing wedge of the lubricating fluid 214 around the outer raceway 208 and across the sensor 20. It is to be appreciated that a particular embodiment of the invention may have 0 to N (N being an integer) number of wipers. If the analyzer 90 (particularly its processor 130) is incorporated into the lubrication sensing device 20 and/or the bearing 22, this incorporation will provide for a substantially autonomous lubrication analysis system. Also, the non-sensor components (electronics, filtering, processing, and/or communications elements) may be located on the exterior surface of the outer raceway 208 and with vias or solderable contact points extending through the outer raceway 208.

Figures 5, 6:
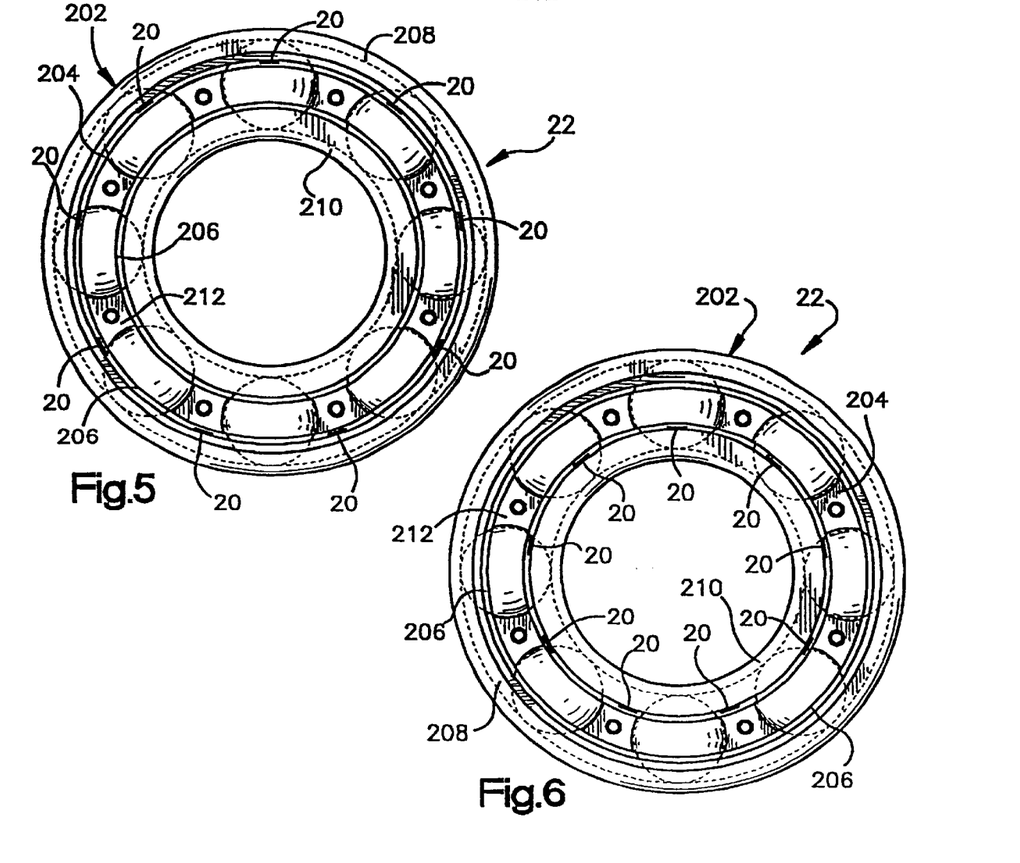

Referring to FIG. 5, a plurality of lubrication sensing devices 20 are mounted on an inner surface of the outer raceway 208. Each of the devices 20 may be mounted in the same manner as the single lubrication sensing device 20 described above in connection with FIG. 4a. Preferably, the sensing devices 20 are equally spaced around the circumference of the outer raceway 208, such as between each rolling element 206. In any event, the use of multiple sensing devices 20 improves analytical accuracy by expanding the range/location of sensor readings, enhances system reliability by redundancy, permits self-diagnosis of the sensors (e.g., a faulty sensor is easily noticed when compared to it's sister sensors), allows the correlation of multiple sensor readings over time (to determine, for example, fluid transport time), and essentially guarantees that different samples of the lubricating fluid 214 are being sensed at least by different sensors. From an economic standpoint, the increased expense of a multiple vs. single lubrication sensing device set-up is approximately equal to the cost of the extra sensing devices per se, since shared processing and/or communication for multiple sensing devices is possible.

Referring to FIG. 6, a plurality of lubrication sensing devices 20 are mounted on an inner surface of the inner raceway 210. As was explained above, in the illustrated bearing 22, the outer raceway 208 is stationary and the inner raceway 210 rotates during operation of the machine. Accordingly, positioning the sensing devices 20 on the inner rotating raceway 210, as compared to the outer non-rotating raceway 208, may permit a faster sampling of the lubricating fluid 214 and over conditions of changing loading. Preferably wireless sensor technology is used to convey information from the sensors for processing so as to avoid having to run electrical connections from the inner raceway 210 to outside the bearing. (Since the exterior surface of the inner raceway 210 is attached to, for example, the rotating shaft 74, such an electrical connection would require the use of slip rings if wireless technology was not employed.) Alternatively, the sensing devices mounted on the inner raceway 210 could communicate to other sensing devices within the bearing 22 to permit realtime, continuous monitoring of the elastohydrodynamic film produced by the lubricating fluid 214.

Figure 7:
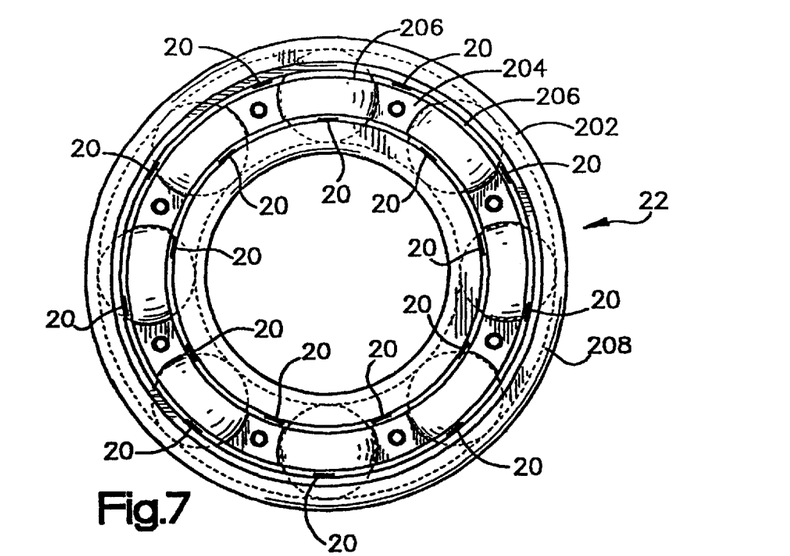

Referring now to FIG. 7, a plurality of lubrication sensing devices 20 are mounted on both the outer raceway 208 and the inner raceway 210. This arrangement would allow the sensing devices 20 on the inner raceway 210 to communicate to the sensing devices 20 on the outer raceway 208. Additionally or alternatively, this arrangement, allows the measurement of the electrical and thermal potential between the outer raceway 208 and the inner raceway 210 thereby providing an indication of bearing and lubricant film conductivity and/or the presence of bearing currents.

Figure 8:
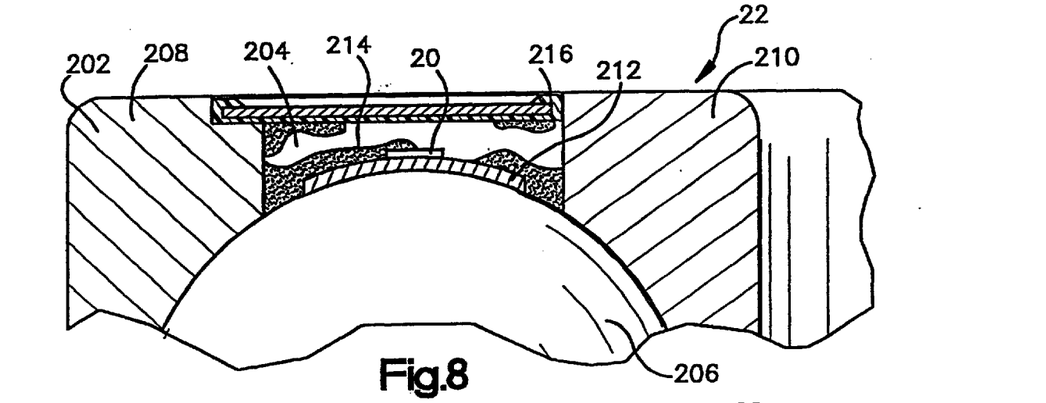

Referring now to FIG. 8, the lubrication sensing device 20 is mounted on the cage 212 of the bearing 22. Mounting the sensing device 20 (or at least the sensors) on the "ball-side" of the cage 212, positions the sensors, in a controlled manner, very close to a moving film of changing lubricant near the surface of the rolling element 206. However, mounting of the sensing device 20 "outside-the ball" side of the cage 212 (as shown) still exposes the sensors to different lubricant locations as the cage 212 traverses around the inner raceway 210 while at the same time minimizing the risk of contact with the adjacent rolling element 206.

Referring now to FIG. 9, the lubrication sensing device 20 is located on the sealing cover 216 of the bearing 22. The sensing device 20 may be attached to a conventional cover or may be incorporated into the cover during its manufacture. In either event, such an arrangement provides for simplified installation and/or replacement of the lubrication sensing device 20. Specifically, an old sealing cover may be removed (usually a relatively inexpensive component as compared to the other components of the bearing, such as the housing 202, the rolling elements 206, and/or the cage 212), and the sealing cover 216 including the lubrication sensing device 20 installed. Also, the lubrication sensing device 20 may be designed (or the sealing cover 21 6 may include additional instrumentation) to detect and pinpoint lubrication-related problems such as lubrication leakage and/or improperly installed or seated sealing covers. For example, a double-sided sensing device 20 could have sensors on its interior surface to sense pH, chemical conditions, electrical conductivity, temperature and/or viscosity and sensors on its exterior surface for detecting lubricant leakage.

Referring to FIG. 10, the lubrication sensing device 20 may be positioned within the outlet pipe 226 of the circulating system 220. This bearing-sensor integration allows the incorporation of a lubrication analysis system by simplifying re-plumbing the circulation pipes thereby leaving the bearing 22 intact. For similar reasons, this bearing-sensor integration simplifies manufacture, installation, testing and field maintenance procedures of the lubrication sensing device(s) 20. Another significant advantage of this embodiment of the invention is the convenience of operably tying the processed sensor data to the circulation control. Specifically, if the processed sensor data reflects that the lubricating fluid 214 is acceptable, the sample of lubricating fluid 214 may flow back through a bypass pipe (not shown) and introduced back into the bearing chamber 204. However, if the processed sensor data reveals that the lubricating fluid 214 is degraded, the bypass may be closed and the pump activated to inject fresh lubricating fluid into the bearing chamber 204 through the inlet pipe 224 until acceptable sensor readings are received. Alternatively, only additives may be introduced into the lube to accommodate depleted additives (such as anti-oxidants) and re-establish proper lube chemistry.

Figure 11:
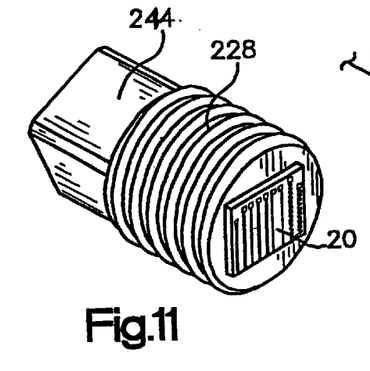
Figure 12:
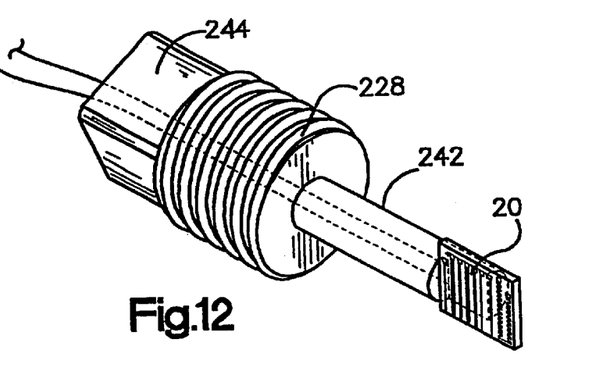

Referring now to FIGS. 11 and 12, the lubrication sensing device 20 is mounted to a cap 228. In the cap-sensor integration shown in FIG. 11, the sensing device 20 is attached directly to the cap 228. In the cap-sensor integration shown in FIG. 12, the sensing device 20 is attached to a probe 242 extending through the cap 228. In either event, such a cap-sensor incorporation provides for simplified installation of the lubrication sensing device 20 by removal of the conventional cap and/or probe and replacement thereof by one including the sensing device 20. Such a cap-sensor integration may be employed in many types of machines employing lubrication and/or fluid reservoirs.

Figure 13:
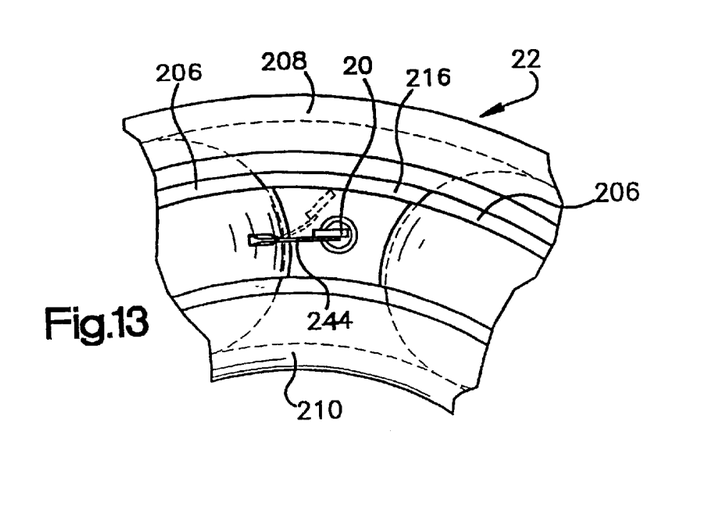

Referring now to FIG. 13, the lubrication sensing device 20 may be mounted on a compliant structure 244 (conceptually like a "rubber policeman") that is geometrically designed to "ride" a moving film surface of lubricant. In this manner, the sensing device 20 (or at least its sensors) may be positioned in close proximity to the moving lubricant film surface (such as adjacent the raceway 208/210 or the cage 212) while at the same time shielding the sensors from direct contact damage. Also, such a bearing-sensor integration allows the distancing of non-sensor electronic elements away from the sensor elements (such as within the compliant structure 244 or within the rigid mounting base).

Figure 14:
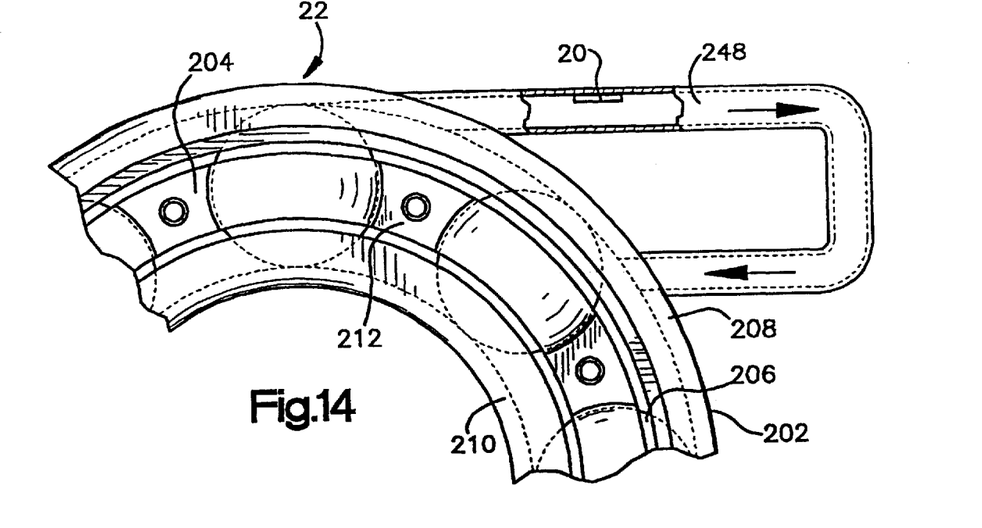

Referring now to FIG. 14, the lubrication sensing device 20 is located within a flowgate 248. The flowgate 248 defines a small bypass channel for diverting a small test or sample amount of lubricating fluid 214 away from the bearing chamber 204 and then reintroducing it back into the bearing chamber 204 once it has flowed past the lubrication sensing device 20. The flowgate 248 is positioned to utilize the moving action of the rolling elements 206 and/or the cage 212 to in effect pump a sample of the lubricating fluid 214 through the bypass channel. This arrangement allows the sensing device 20 be positioned away from the moving components of the bearing 22 (e.g., the rolling elements 206 and the cage 212) while at the same time providing for a continuous exchange of lubricant flowing past the sensing device 20. The bypass channel may be much smaller than shown in FIG. 14 and effectively integrated within the outer race 208 of the bearing.

Figure 15:
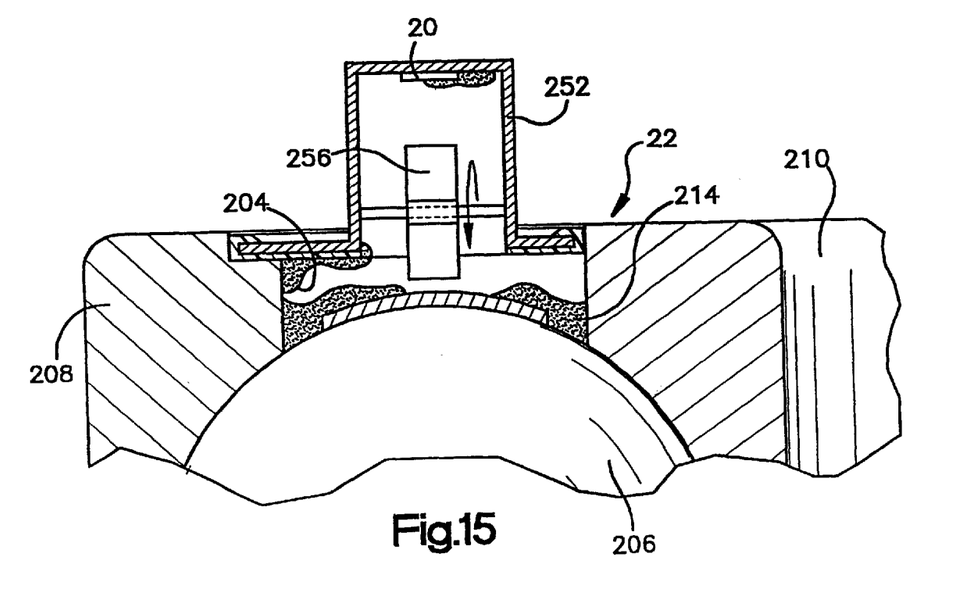

Referring now to FIG. 15, the lubrication sensing device 20 is located within a small reservoir 252 which communicates with, but is positioned outside, the bearing chamber 204. A rotating paddle 256 (essentially a miniature paddlewheel or propeller having a hub rotatably mounted to the bearing and paddles projecting radially outward from the hub) is provided so that it spins as the rolling elements 206 and the cage 212 rotate thereby and/or as the lubricating fluid 214 is circulated thereby. In this manner, the sensing device 20 is constantly presented with untested samples of the lubricating fluid 214 while at the same time the sensing device 20 is physically isolated from the moving bearing components. This bearing-sensor integration may allow a more "rugged" mounting of the sensing device 20, a more precise positioning of the device 20 in relation to the moving lubricating fluid, easier integration of sensing and electronics components, a mechanical base for self-powered operation, and/or simplified integration of the sensor 20 into the bearing 22.

In connection with the bearing-sensor integrations shown in FIGS. 4–15 (and also in connection with any other bearing-sensor integrations possible with and contemplated by the present invention), the reliability and credibility of the processed results depends initially on the sensor readings accurately reflecting the true state of the lubricating fluid 214. Specifically, if the sensors are repeatedly sensing the parameters of only a small static portion of the lubricating fluid 214, rather than the lubricating fluid as a whole, the most advanced and sophisticated processing procedures may not be able to provide an accurate analysis. For this reason, it may be important that untested samples of the lubricating fluid 214 be continuously encountered by the sensing device(s) 20. In certain bearing-sensor integrations, this is accomplished by the use of a plurality of sensing devices 20 (see, e.g., FIGS. 5–7), the positioning of the sensing device(s) 20 on or near a moving component of the bearing 22 (see e.g., FIGS. 6–8 ), and/or the positioning of the sensing device(s) in locations of force fluid flow (see e.g., FIGS. 10–13).

In addition to the positioning of the sensing device(s), the use of certain supplementary fluid transporting mechanisms may be necessary or desirable. For example, the wiper arm 240 in the bearing-sensor integration shown in FIG. 4a or the paddle 256 in the bearing-sensor integration shown in FIG. 15, may be used to insure that the sensing device(s) 20 are continuously exposed to dynamic samples of the lubricating fluid 214. These transport mechanisms may be duplicated, modified, and/or combined for use in other bearing-sensor integrations. Additionally or alternatively, other actuators may be used to transport untested lubricant over the sensing elements. For example, an array of cilia-like coordinated actuators mounted within the bearing 22 may provide the necessary or desired transport arrangement. Other appropriate transport devices include MEMs valves, pumps, and micro-fluidic devices that could be integrated with the sensing devices 20.

One may now appreciate that the present invention provides an integration of the lubrication sensing device 20 into the bearing 22 so that a substantially high data sampling rate can be obtained and highly accurate, real-time, continuous up-to-date data analysis of lubrication health may be provided. In this manner, lubrication maintenance can be scheduled to correspond precisely with the state of the lubrication and/or the processed data can be compiled for trend analysis and forecasting. The time-based expected rate of lube degradation can be used to predict when re-lubrication or other related maintenance action (e.g. replace worn seals) is required. This provides a solid basis for reliable condition-based maintenance directed at one of the most critical, high-maintenance, and failure-prone components in rotating machinery. Although the invention has been and described with respect to certain preferred embodiments, it is obvious that equivalent alterations and modifications will occur to others skilled in the art upon a reading and understanding of this specification. The present invention includes all such equivalent alterations and modifications and is limited only by the scope of the following claims.

What is claimed is:

1. A bearing-sensor integration comprising a bearing and at least one lubrication sensing device;
   the bearing comprising a bearing housing defining a chamber, a plurality of rolling elements retained within the chamber, and lubricating fluid contained within the chamber;
   the lubrication sensing device comprising a plurality of different sensors;
   the lubrication sensing device being positioned relative to the bearing so that the sensors sense in situ different parameters of the lubricating fluid, at least one of the plurality of different sensors being adapted to sense a parameter other than one directly related to one of temperature and thermal response of the lubricating fluid.

2. A bearing-sensor integration as set forth in claim 1 comprising a plurality of lubrication-sensing devices positioned at different locations relative to the bearing to sense in situ certain parameters of the lubricating fluid.

3. A bearing-sensor integration as set forth in claim 2 wherein the lubrication sensing devices communicate with each other.

4. A lubrication analysis system comprising the bearing-sensor integration set forth in claim 1 and a data collecting processor; the processor receiving lubrication-related data from the lubrication sensing device, processing the lubrication-data, and providing information relating to lubrication health.

5. A lubrication analysis system as set forth in claim 4 wherein the lubrication sensing devices communicates with the processor in a wireless manner.

6. A bearing-sensor integration as set forth in claim 1 wherein the bearing housing comprises a raceway and wherein the lubrication sensing device is positioned on an interior surface of the raceway.

7. A bearing-sensor integration as set forth in claim 2 wherein the bearing housing comprises a raceway and wherein the plurality of lubrication sensing devices are positioned on an interior surface of the raceway.

8. A bearing-sensor integration as set forth in claim 6 wherein the raceway is an outer raceway.

9. A bearing-sensor integration as set forth in claim 6 wherein the raceway is an inner raceway.

10. A bearing-sensor integration as set forth in claim 2 wherein the bearing housing comprises an outer raceway and an inner race, wherein at least one lubrication sensing device is positioned on the outer raceway and at least one lubrication sensing device is positioned on the inner raceway.

11. A bearing-sensor integration as set forth in claim 10 wherein the lubrication sensing device positioned on the inner raceway communicates with the lubrication sensing device positioned on the outer raceway.

12. A lubrication analysis system including the bearing-sensor integration set forth in claim 10 and a processor and wherein the processor receives lubrication-related data from the lubrication sensing devices and makes inner-outer comparison between the lubrication-related data received from the lubrication sensing device positioned on the inner raceway and the lubrication-related data received from the lubrication sensing device positioned on the outer raceway.

13. A bearing-sensor integration as set forth in claim 1 wherein the bearing further comprises a cage which retains the rolling elements within the bearing chamber and wherein the lubrication sensing device is positioned on the cage.

14. A bearing-sensor integration as set forth in claim 1 wherein the bearing further comprises a sealing cover which seals the lubricating fluid within the chamber and wherein the lubrication sensing device is positioned on the sealing cover.

15. A bearing-sensor integration as set forth in claim 14 wherein the lubrication sensing device includes a sensor which detects the presence of leakage on an exterior side of the sealing cover.

16. A bearing-sensor integration as set forth in claim 1 wherein the bearing further comprises a circulating system which introduces fresh lubricating fluid or additives into the bearing chamber and wherein the lubrication sensing device is mounted to sense a portion of the lubricating fluid flowing through the circulating system.

17. A bearing-sensor integration as set forth in claim 16 wherein the circulating system flushes used lubricating fluid from the bearing chamber through an outlet pipe and wherein the lubrication sensing device is mounted to sense a portion of the lubricating fluid flowing through the circulating system.

18. A lubrication analysis system comprising the bearing-sensor integration set forth in claim 16 and a processor and wherein the processor receives lubrication-related data from the lubrication sensing device and controls the circulating system to introduce fresh lubricating fluid into the bearing chamber as a result of the received and analyzed lubrication-related data.

19. A bearing-sensor integration as set forth in claim 16 wherein the circulating system includes an inlet pipe and wherein the lubrication sensing device is mounted to sense a portion of the lubricating fluid in the inlet pipe.

20. A bearing-sensor integration as set forth in claim 19 wherein the inlet pipe includes a cap at one end and wherein the lubrication sensing device is mounted to the cap.

21. A bearing-sensor integration as set forth in claim 19 wherein the inlet pipe includes a probe passing therein and wherein the lubrication sensing device is mounted to the probe.

22. A bearing-sensor integration as set forth in claim 1 further comprising a compliant structure positioned within the bearing chamber and wherein the lubrication sensing device is mounted to the compliant structure.

23. A bearing-sensor integration as set forth in claim 1 wherein the bearing further comprises a flowgate through which a portion of the lubricating fluid is temporarily diverted away from the bearing chamber and wherein the lubrication sensing device is positioned to sense the portion of the lubricating fluid in the flowgate.

24. A bearing-sensor integration as set forth in claim 1 wherein the bearing further comprises a reservoir which communicates with but is positioned outside the bearing chamber and into which a portion of the lubricating fluid flows and wherein the lubrication sensing device is positioned to sense the portion of the lubricating fluid in the reservoir.

25. A bearing-sensor integration as set forth in claim 1 further comprising a transport mechanism that transports a portion of the lubricating fluid towards the sensors of the lubrication sensing device.

26. A bearing-sensor integration as set forth in claim 1 wherein the transport mechanism comprises a wiper arm having one end pivotally attached to the bearing whereby unattached portions of the wiper arm pivot to transport a portion of the lubricating fluid towards the sensors of the lubrication sensing device.

27. A bearing-sensor integration as set forth in claim 1 wherein the transport mechanism comprises a hub rotatably mounted to the bearing and paddles projecting radially outward from the hub whereby the paddles rotate to transport a portion of the lubricating fluid towards the sensors of the lubrication sensing device.

28. A bearing sensor integration as set forth in claim 1 where the sensors are self-powering based upon presence of a rotating magnetic field.

29. A bearing-sensor integration as set forth in claim 1 wherein at least some of the sensors of the lubrication sensing device are selected from the group consisting of:
 a pH sensor;
 a chemical sensor;
 an electrical conductivity sensor;
 a temperature sensor; and
 a viscosity sensor.

30. A bearing-sensor integration as set forth in claim 29 wherein the sensors are formed on a silicon base.

31. A bearing-sensor integration as set forth in claim 30 wherein the sensors are formed on both sides of the silicon base.

32. A bearing-sensor integration as set forth in claim 30 wherein the sensors are formed on a flexible base.

33. A bearing-sensor integration as set forth in claim 30 wherein the sensors are printed on the bearing.

34. A bearing lubrication analysis system, comprising:
 a bearing employing a lubricant;
 first sensing means for sensing a first parameter of the lubricant;
 second sensing means for sensing a second parameter of the lubricant; and
 processing means operatively coupled to the first and second sensing means, the processing means analyzing the sensed lubricant parameters, at least one of the first sensing means and the second sensing means being adapted to sense a parameter other than one directly related to one of temperature and thermal response of the lubricating fluid.

35. The system of claim 34, wherein the first lubricant parameter is one of: pH, chemistry, electrical conductivity, temperature, and viscosity.

36. The system of claim 34, wherein the second lubricant parameter is one of: pH, chemistry, electrical conductivity, temperature, and viscosity.

37. A bearing-sensor integration, comprising:
 a bearing employing a lubricant; and
 a lubricant sensor integrated with the bearing such that at least a portion of the sensor is in contact with the lubricant, the lubricant sensor further including:
 a pH sensor;
 a chemical sensor;
 an electrical conductivity sensor; and
 a temperature sensor.

38. A method for determining the health of a bearing lubricant, comprising the steps of:
 using a lubricant sensor operatively coupled to a bearing to collect in situ data relating to at least one lubricant parameter, the at least one lubricant parameter being selected from a group including: pH, chemistry, electrical conductivity, temperature and viscosity; and
 using a processor operatively coupled to the lubricant sensor to analyze the data and render a health assessment of the lubricant.

39. A method for determining the health of a bearing lubricant, comprising the steps of:
 using a lubricant sensor operatively coupled to a bearing to collect in situ data relating to at least one lubricant parameter, the at least one lubricant parameter being selected from or determined as a function of a group of lubricant properties including at least two of: pH, chemistry, electrical conductivity, temperature and viscosity; and
 using a processor operatively coupled to the lubricant sensor to analyze the data and render a health assessment of the lubricant.

40. A drain plug/lubricant sensor combination arranged for use in analyzing a lubricant health condition data in a mechanical equipment lubrication application; comprising:
 a drain plug of a lubricant reservoir, the drain plug including a first end and a second end; and
 a lubricant sensor coupled to the surface of the first end of the drain plug, at least a portion of the lubricant sensor being in contact with the lubricant, the lubricant sensor including a pH sensor, a chemical sensor, an electrical conductivity sensor, and a temperature sensor.

41. The drain plug/lubricant sensor combination of claim 40, the lubricant sensor further including a viscosity sensor.

* * * * *